(12) United States Patent
Zhang et al.

(10) Patent No.: US 9,920,292 B2
(45) Date of Patent: Mar. 20, 2018

(54) SYSTEM AND METHOD FOR INITIATING A CELL CULTURE

(71) Applicant: General Electric Company, Schenectady, NY (US)

(72) Inventors: Chengkun Zhang, Niskayuna, NY (US); Reginald Donovan Smith, Schenectady, NY (US); Kenneth Roger Conway, Clifton Park, NY (US); Anshika Bajaj, Redmond, WA (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 226 days.

(21) Appl. No.: 14/841,072

(22) Filed: Aug. 31, 2015

(65) Prior Publication Data
US 2017/0058252 A1    Mar. 2, 2017

(51) Int. Cl.
C12M 1/02 (2006.01)
C12Q 3/00 (2006.01)
C12M 3/00 (2006.01)
C12M 1/00 (2006.01)
(Continued)

(52) U.S. Cl.
CPC ............ *C12M 41/22* (2013.01); *C12M 21/08* (2013.01); *C12M 23/14* (2013.01); *C12M 23/38* (2013.01); *C12M 23/48* (2013.01); *C12M 27/16* (2013.01); *C12M 29/24* (2013.01); *C12M 41/48* (2013.01); *C12Q 3/00* (2013.01)

(58) Field of Classification Search
CPC ...... C12M 23/14; C12M 23/48; C12M 23/38; C12M 29/24; C12M 27/16; C12M 41/22; C12M 41/48; C12M 21/08; C12Q 3/00
See application file for complete search history.

(56) References Cited

U.S. PATENT DOCUMENTS

| 5,443,985 A | 8/1995 | Lu et al. |
| 6,399,375 B2 | 6/2002 | Vajta |
| 7,317,989 B2 | 1/2008 | DiFoggio et al. |

(Continued)

FOREIGN PATENT DOCUMENTS

| CA | 2 801 768 A1 | 7/2014 |
| CN | 201485460 U | 5/2010 |

(Continued)

OTHER PUBLICATIONS

Fochtmann, J.; Peters, C.; Fernandez, R.; Lucklum, R.; McCann, D.; Vetelino, J.; Arnau, A.; "Optimization of the lateral field excited platform for liquid sensing applications", Sens. Actuators B 2012, 170, 95-103.

(Continued)

*Primary Examiner* — Michael Hobbs
(74) *Attorney, Agent, or Firm* — Pabitra K. Chakrabarti

(57) ABSTRACT

System and methods are provided for initiating a cell culture. The systems and methods include a first enclosure containing a thermal mass positioned on a surface area of a platform. The systems and methods include a second enclosure, containing a culture fluid and a gas mixture, placed on the first enclosure such that the first enclosure is positioned between the second enclosure and the platform. The systems and methods further include a cover secured on the second enclosure, and generating first thermal energy on the surface area of the platform and second thermal energy from the cover.

20 Claims, 4 Drawing Sheets

(51) Int. Cl.
*C12M 3/06* (2006.01)
*C12M 1/36* (2006.01)

(56) References Cited

U.S. PATENT DOCUMENTS

| | | | |
|---|---|---|---|
| 7,562,557 B2 | 7/2009 | Bennett et al. | |
| 7,629,167 B2 | 12/2009 | Hodge et al. | |
| 7,911,345 B2 | 3/2011 | Potyrailo et al. | |
| 8,318,099 B2 | 11/2012 | Potyrailo et al. | |
| 8,468,871 B2 | 6/2013 | Potyrailo et al. | |
| 8,475,716 B2 | 7/2013 | Potyrailo et al. | |
| 8,569,060 B2 | 10/2013 | Timmins et al. | |
| 8,643,388 B2 | 2/2014 | Hedges | |
| 8,710,973 B2 | 4/2014 | Schneider et al. | |
| 8,732,938 B2 | 5/2014 | Kolosov et al. | |
| 8,833,145 B2 | 9/2014 | Fischer et al. | |
| 2007/0127901 A1* | 6/2007 | Kuzyk | H05B 3/82 392/446 |
| 2007/0269888 A1* | 11/2007 | Houtzager | B01F 11/0017 435/252.1 |
| 2009/0035856 A1 | 2/2009 | Galliher et al. | |
| 2009/0120169 A1 | 5/2009 | Chandler, Jr. et al. | |
| 2010/0075405 A1 | 3/2010 | Broadley et al. | |
| 2010/0261226 A1 | 10/2010 | Niazi | |
| 2011/0117538 A1 | 5/2011 | Niazi | |
| 2011/0207170 A1 | 8/2011 | Niazi | |
| 2012/0231504 A1 | 9/2012 | Niazi | |
| 2012/0258441 A1 | 10/2012 | Gebauer et al. | |
| 2012/0260671 A1 | 10/2012 | Damren et al. | |
| 2013/0196276 A1 | 8/2013 | Lee et al. | |
| 2013/0288346 A1 | 10/2013 | Tuohey et al. | |
| 2014/0106453 A1 | 4/2014 | Kunas et al. | |
| 2014/0193883 A1 | 7/2014 | Eriksson et al. | |

FOREIGN PATENT DOCUMENTS

| | | |
|---|---|---|
| CN | 203923208 U | 11/2014 |
| EP | 1 434 856 B1 | 7/2013 |
| WO | 2011/078773 A1 | 6/2011 |
| WO | 2013/106809 A1 | 7/2013 |
| WO | 2014/204384 A1 | 12/2014 |
| WO | 2015/048764 A2 | 4/2015 |

OTHER PUBLICATIONS

MacDonald, J.R.; "Impedance spectroscopy", Ann. Biomed. Eng. 1992, 20, 289-305.

Guan, L.; Feng, X.L.; Xiong, G.; "Engine lubricating oil classification by SAE grade and source based on dielectric spectroscopy data", Anal. Chim, Acta 2008, 628, 117-120.

Pejcic, B.; De Marco, R.; "Impedance spectroscopy: Over 35 years of electrochemical sensor optimization", Electrochim. Acta 2006, 51, 6217-6229.

De Souza, J.E.; Scherer, M.D.; Caceres, J.A.S.; Glares, A.R.L.; M'Peko, J.-C.; "A close dielectric spectroscopic analysis of diesel/biodiesel blends and potential dielectric approaches for biodiesel content assessment", Fuel Cells 2013, 105, 705-710.

Liu, Y.; Difoggio, R.; Sanderlin, K.; Perez, L.; Zhao, J.; "Measurement of density and viscosity of dodecane and decane with a piezoelectric tuning fork over 298-448 K and 0.1-137.9 MPa", Sens. Actuators A 2011, 167, 347-353.

Guan, L.; Feng, X.L.; Xiong, G.; Xie, J.A.; "Application of dielectric spectroscopy for engine lubricating oil degradation monitoring", Sens. Actuators A 2011, 168, 22-29.

Capone, S.; Zuppa, M.; Presicce, D.S.; Francioso, L.; Casino, F.; Siciliano, P.; "Metal oxide gas sensor array for the detection of diesel fuel in engine oil", Sens. Actuators B 2008, 131, 125-133.

Wang, W.; Zhang, C.; Liu, Y.; Ding, T.; "Impedance analysis for lateral field excited acoustic wave sensors", Sens. Actuators B 2011, 156, 969-975.

Soleimant, M.; Sophocleous, M.; Wang, L.; Atkinson, J.; Hosier, I.L.; Vaughan, A.S.; Taylor, R.I.; Wood, R.J.K.; "Base oil oxidation detection using novel chemical sensors and impedance spectroscopy measurements", Sens. Actuators B 2014, 199, 247-258.

Zhu, X.; Du, L.; Zhe, J.; "An integrated lubricant oil conditioning sensor using signal multiplexing", J. Micromech. Microeng. 2015, 25, 015006.

McCann, D.F.; Frenc Jr., L.A.; Wark, M.S.; Vetelino, J.F.; "Recent advances in lateral field excited and monolithic spiral coil acoustic transduction bulk acoustic wave sensor platforms", Meas. Sci. Tech. 2009, 20, art. No. 124001.

Hempel, U.; Schneider, T.; Doerner, S.; Lucklum, R.; Hauptmann, P.R.; Vetelino, J.F.; "Application of a portable RF impedance spectrum analyzer for the investigation of lateral field excited acoustic wave sensors in a liquid environment", Proceedings—IEEE Ultrasonics Symposium 2007, 373-376.

Hempel, U; Lucklum, R.; Hauptmann, P.; Eernisse, E.P.; Puccio, D.; Fernandez Diaz, R.; Vives, A. A.; "Lateral field excited quartz crystal resonator sensors for determination of acoustic and electrical properties of liquids", IEEE International Frequency Control Symposium 2008, 705-710.

Cho, J.; Park, S.; "Capacitive sensor for automotive engine oil degradation using wireless network", International Symposium on Advanced Packaging Materials: Microtech, APM '10 2010, 88-91.

Toledo, J.; Manzaneque, T.; Hernando-Garcia, J.; Vazquez, J.; Ababneh, A.; Seidel, H.; Lapuerta, M.; Sanchezrojas, J.L.; "Application of quartz tuning forks and extensional microresonators for viscosity and density measurements in oil/fuel mixtures", Microsyst. Technol. 2014, 20, 945953.

Buhrdorf, A.; Dobrinski, H.; Ludtke, O.; Bennett, J.; Matsiev, L.; Whrich, M.; Kolosov, O.; "Multiparameteric Oil Condition Sensor Based on the Tuning Fork Technology for Automotive Applications", In Advanced Microsystems for Automotive Applications 2005; J. Valldorf and W. Gessner, Ed.; Springer: 2005; 289-298.

Latif, U.; Dickert, F.L.; "Conductometric sensors for monitoring degradation of automotive engine oil"; Sensors 2011, 11, 8611-8625.

Perez, A.T.; Hadfield, M.; "Low-cost oil quality sensor based on changes in complex permittivity", Sensors 2011, 11, 10675-10690.

Database WPI Week 201040, Thomson Scientific, London, GB, AN 2010-G58165, XP002764114, pp. 1-2 (2010).

Wernli, U., et al., "CD 293 AGT™ medium for the cultivation of HEK 293 EBNA Cells in small-scale bioreactors: an application report," Quest, vol. 5, issue 1, pp. 18-21 (2008).

International Search Report and Written Opinion issued in connection with corresponding PCT Application No. PCT/EP2016/070142 dated Nov. 24, 2016

* cited by examiner

SYSTEM AND METHOD FOR INITIATING A CELL CULTURE

FIELD

One or more embodiments of the subject matter described herein generally relates to systems and methods for temperature and osmolality control of a cell culture or media.

BACKGROUND

A bioreactor provides closed loop controlled environments to promote growth or cultivation of cells. During the cultivation process, cells are combined with a culture medium or media to form a cell culture within a bag. The bioreactor controls an agitation process, maintains a temperature and pH of the media, gas mixture and flow within the bag, and/or the like for cultivation and growth of the cells over time (e.g., hours, days).

However, conventional bioreactors typically require at least a minimum volume, such as two hundred milliliters (mL) or more of cell culture within the bag. Cells within the bag having a culture under the minimum volume can be killed by the functions of the bioreactor. For example, the cell culture can over heat and/or have wide temperature fluctuations by the bioreactor maintaining the temperature of the cell culture due to the reduced thermal mass of the cell culture within the bag, killing cells within the cell culture. Additionally, due to the low volume within the bag, condensate accumulating within the bag has a greater effect on the osmolality increase of the cell culture due to the loss of water. For example, the condensate accumulating within the bag increases the osmolality of the media affecting cell growth and/or may kill cells within the cell culture.

Thus, before using the bioreactor, an operator must scale up cultures from an initial volume, such as fifty mL to the minimum volume of the bioreactor. Conventionally, the operator scales up the cell culture within a static environment using a static culture vessel, such as a T-flask manipulated under a sterile hood and maintained in an incubator, until the culturing volume grows to the minimum requirement of the bioreactor. The initial phase of a culture before a bioreactor expansion consist of many open transfer manual steps (e.g., under the sterile hood) for scaling up cultures from the initial volume to a final volume or cell number suited for transfer into the bioreactor. Further, when the minimum volume is reached, the operator may transfer the cell culture into the bag for the bioreactor. The transfer process increases the risk of contamination and/or risks to the cell population. Accordingly, a method and/or system is needed for a more efficient and closed way to initiate a cell culture for cell cultivation.

BRIEF DESCRIPTION

In an embodiment a bioreactor system is provided. The system includes a platform generating first thermal energy on a surface area of the platform. The system also includes a first enclosure containing a thermal mass. The first enclosure is positioned adjacent to the surface area, and absorbs at least some of the first thermal energy from the platform. The system also includes a second enclosure containing a culture fluid and a flowing gas mixture. The first enclosure is positioned between the second enclosure and the platform. The thermal mass is thermally coupled to the culture fluid. The system also includes a cover positioned on the second enclosure. The cover generating second thermal energy, and is thermally coupled to the gas mixture in the headspace of the second enclosure.

In an embodiment a method is provided. The method includes positioning a first enclosure on a surface area of the platform. The first enclosure containing a thermal mass. The method also includes placing a second enclosure on the first enclosure such that the first enclosure is positioned between the second enclosure and the platform. The second enclosure containing a culture fluid and a gas mixture. The method also includes securing a cover on the second enclosure, and generating first thermal energy on the surface area of the platform and second thermal energy from the cover. A temperature of the cover based from the second thermal energy is more than a temperature of the platform based from the first thermal energy.

In an embodiment a bioreactor system is provided. The system includes a platform pivotably mounted on a base such that the opposing edges of the platform rotate about an axis of the base resulting in a rocking motion. The platform generating first thermal energy on a surface area of the platform during the rocking motion. The system also includes a first enclosure containing a thermal mass, and is positioned adjacent to the surface area of the platform. The thermal mass absorbing at least some of the first thermal energy generated from the platform. The system also includes a second enclosure containing a culture fluid and a gas mixture. The first enclosure is positioned between the second enclosure and the platform. The thermal mass of the second enclosure is thermally coupled to the culture fluid such that the culture fluid absorbs at least some thermal energy from the first enclosure. The system also includes a cover positioned on a top surface area of the second enclosure such that the cover is thermally coupled to the gas mixture. The cover generating second thermal energy that is absorbed by the second enclosure without altering the set temperature of the culture.

DETAILED DESCRIPTION

Figure 1:
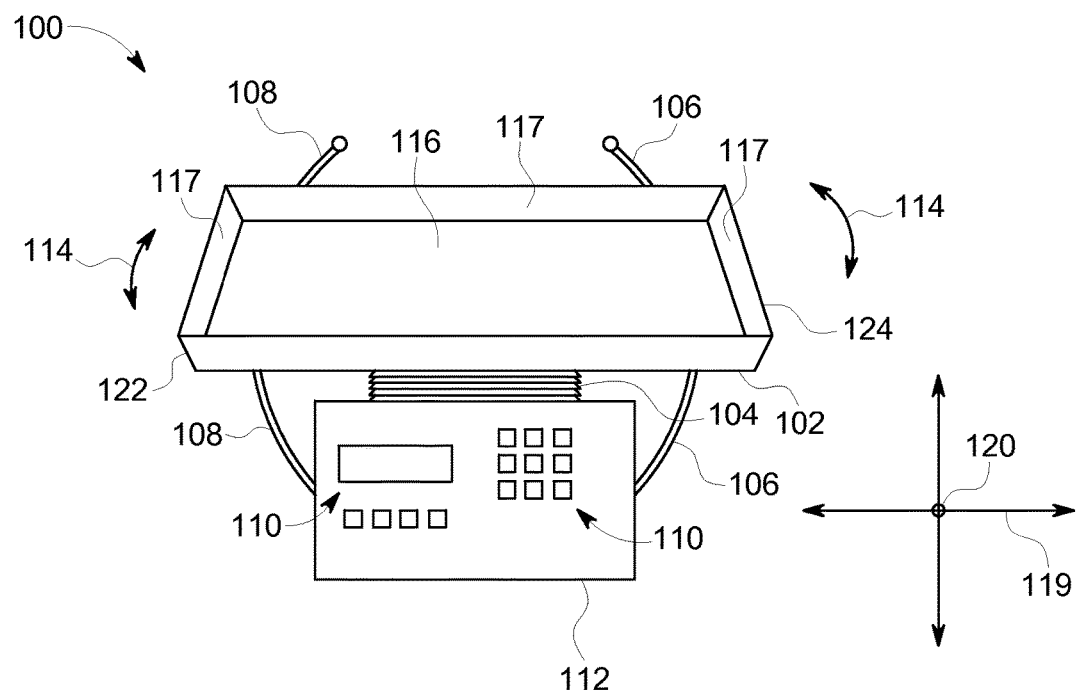
FIG. 1 is an illustrative diagram of a bioreactor system, in accordance with an embodiment.

Various embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, any programs may be stand-alone programs, may be incorporated as subroutines in an operating system, may be functions in an installed software package, and the like. It should be understood that the various embodiments are not limited to the arrangements and instrumentality shown in the drawings.

As used herein, the terms "system," "unit," "subsystem," or "module" may include a hardware and/or software system that operates to perform one or more functions. For example, a module, unit, subsystem, or system may include a computer processor, controller, or other logic-based device that performs operations based on instructions stored on a tangible and non-transitory computer readable storage medium, such as a computer memory. Alternatively, a module, unit, subsystem, or system may include a hard-wired device that performs operations based on hard-wired logic of the device. The modules or units shown in the attached figures may represent the hardware that operates based on software or hardwired instructions, the software that directs hardware to perform the operations, or a combination thereof. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Generally, various embodiments provide methods and systems for initiating a cell culture using the automated systems of a conventional bioreactor system. The selected cells from a source material (e.g., T cells from blood) may be combined with a culture medium or media, which promotes cell growth. The selected cells with the culture medium from a culture fluid or media having an initial volume, such as fifty milliliters (mL). The culture medium may include Human AB serum, penicillin-streptomycin, Glutamax, Interleukin 2, NAC, and/or the like. The cell culture may be contained within an enclosure, which is also inflated with a gas mixture. The gas mixture may include nitrogen, oxygen, carbon dioxide, and/or the like, which interacts with the cell culture, for example, affecting a pH level of the cell culture. The enclosure may be made from a polymeric material, such as a plastic film or laminate, which allows for heat transfer between the cell culture and the exterior surface of the enclosure.

The enclosure may be positioned on top of a thermal mass contained within a separate enclosure. The enclosure containing the thermal mass is positioned or sandwiched between a heating plate of the bioreactor system and the enclosure containing the cell culture. The thermal mass may include a liquid having a high thermal capacity such as water, ethylene glycol, diethylene glycol, ammonia, and/or the like. The thermal mass has a larger volume than the cell culture. For example, the thermal mass may have a volume above the minimum volume requirement of the bioreactor system, such as a volume of three hundred milliliters. The thermal mass performs as a heat flux buffer between the cell culture and the heating plate.

Additionally, a cover is positioned atop of the enclosure and is overlaid on a top portion of the enclosure adjacent to the gas mixture. The cover may generate heat to increase a temperature of the top portion above a dew point of the enclosure of the cell culture. The cover prevents and/or reduces condensate from forming on the top surface of the enclosure reducing a chance of increasing osmolality of the cell culture due to loss of water.

At least one technical effect of various embodiments allow for initiating a cell culture using a conventional bioreactor without making hardware and/or software modifications to the conventional bioreactor. At least one technical effect of various embodiments include reducing labor costs for initiating a cell culture. At least one technical effect of various embodiments include allowing aseptic transfer of the cell culture between enclosures.

FIG. 1 is a perspective illustration of a bioreactor system 100. Optionally, a portion of the bioreactor system 100 may be similar to the WAVE Bioreactor™ Systems by GE Healthcare. The bioreactor system 100 includes a platform 102. The platform 102 may include a surface area 116 surrounded by raised edges 117. The surface area 116 may be formed by a thermally conductive material or alloy, such as aluminum, copper, silver, gold, stainless steel, steel, iron, a metal composite, and/or the like. The raised edges 117 may aid in securing an enclosure (e.g., first enclosure 320 of FIG. 3) positioned on the surface area 116 of the platform 102. The platform 102 may be pivotably mounted on a base 112 using a pivot or pivot point 104 allowing the platform to rock back and forth across the pivot point 104. For example, the opposing edges 122 and 124 of the platform 112 may adversely rotate along the arrows 114 about an axis 120 of the base 112.

Figure 2:
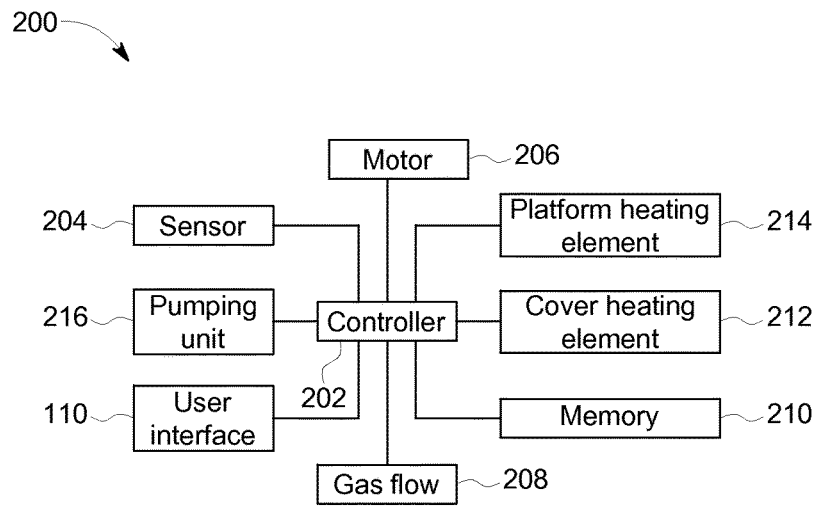
FIG. 2 is a schematic diagram of the bioreactor system of FIG. 1.

The base 112 may enclose electrical and/or control components, such as the components shown in FIG. 2, of the bioreactor system 100. FIG. 2 is a schematic block diagram 200 of the bioreactor system 100. The controller circuit 202 may include one or more processors, a central processing unit (CPU), a microprocessor, and/or any other electronic component capable of processing inputted data according to a specific logical instruction. For example, the controller circuit 202 may execute program instructions that are stored on memory 210 to perform one or more programmed operations. The memory 210 may include RAM, ROM, EEPROM, and/or other tangible and non-transitory computer readable medium. Additionally or alternatively, the memory 210 may be integrated with the controller circuit 202.

The controller circuit 202 may be electrically and/or communicatively coupled to a sensor 204, a motor 206, a user interface 110, gas flow interface 208, the memory 210, a platform heat generator, a cover heating element interface 212, and a pumping unit 216.

The motor 206 may be configured to control and/or adjust a position of the platform 102 with respect to the base number 112 based on instructions received by the controller circuit 202. The motor 206 may be an electric motor, an actuator, and/or other electromechanical device. The motor 206 may control a rocking speed and angle of the platform 102 for agitating (e.g., displacing) a cell culture positioned on the platform 102. The rocking speed may correspond to a rate at which the opposing edges 122 and 124 move adversely along the arrows 114. The angle of the platform 102 may correspond to a maximum angular or distance an opposing edge 122 and 124 may travel along the arrows 114, respectively, before changing direction. For example, the rocking speed may be two rocks per minute at an angle of two degrees relative to a horizontal plane 119. It should be noted that in other embodiments the rocks per minute and angle may be greater than and/or less than two, respectively.

The sensor 204 may be a temperature sensor such as a thermocouple, thermistor, and/or the like. The sensor 204 may be positioned and/or configured to measure a temperature of a thermal mass (e.g., the thermal mass 304 of FIG. 3) on top of the platform 102. For example, the sensor 204 may be positioned proximate to and/or in contact with the thermal mass 304. Temperature measurements of the sensor 204 may be received by the controller 202 and/or compared by the controller 202 to a predetermined temperature target. For example, the predetermined temperature target may be 37.5 degrees Celsius. It should be noted in other embodiments, the predetermined temperature target may be greater than or less than 37.5 degrees Celsius. (e.g., 37 degrees Celsius) In another embodiment, the predetermined temperature target may be a range about a set point. For example, the predetermined temperature target may be a 0.2 degree Celsius range about 37.5 degrees Celsius. Based on the temperature measurements of the sensor 204 with respect to the predetermined temperature target, the controller 202 may adjust an amount of thermal energy generated by the platform 102.

The user interface 110 may include a keypad, a display, a keyboard, a touchscreen, tactile buttons, and/or the like for sending various instructions to the controller circuit 202. For example, the controller circuit 202 may receive instructions to increase the rocks per minute of the platform based on instructions received from the user interface 110. The user interface 110 may be positioned on an outer surface of the base 112, as shown in FIG. 1. Additionally or alternatively, the user interface 110 may be positioned on the platform and/or remote from the base 112 (e.g., a computer communicatively coupled to the bioreactor system 100).

The gas flow interface 208 may be configured to control a flow rate of one or more gases carried by a plurality of elongated tubes 106 and 108 (shown in FIG. 1) from one or more tanks or containers (not shown) to an enclosure (e.g., a second enclosure 306 shown in FIG. 4), which is absorbed by the cell culture. The gas flow interface 208 may be a flow limiter, a mass flow controller, a gas pump and/or the like. The one or more tanks may supply one or more gases, which are carried by the elongated tubes 106 and 108. For example, one or more tanks may contain one or more gases, such as nitrogen, oxygen, carbon dioxide, and/or the like, which are delivered or carried by the elongated tubes 106 and 108. Optionally, the gas flow interface 208 may combine and/or mix gases from one or more tanks into a gas mixture, which is carried by one or more of the elongated tubes 106 and 108.

The gas flow interface 208 may receive instructions from the controller circuit 202 to regulate an amount of gas within an enclosure coupled to the elongated tubes 106 and 108. For example, the elongated tube 106 may deliver a gas mixture of oxygen, carbon dioxide and/or nitrogen into an enclosure (e.g., the second enclosure 306), and the elongated tube 108 may exhaust the gas mixture from the enclosure to circulate the gas mixture within the enclosure.

In various embodiments, the gas flow interface 208 may control a gas flow rate and/or circulation of the gas mixture within the enclosure (e.g., the second enclosure 306) based on instructions received by the controller 202. For example, the delivery and exhaust of the gas mixture via the elongated tubes 106 and 108, respectively, may displace portions of the gas mixture by circulating the gas mixture or move the gas mixture within the enclosure between the elongated tubes 106 and 108. The controller 202 may instruct the gas flow interface 208 reach a gas flow rate within the enclosure based on a gas requirement of the cell culture.

Optionally, the gas flow rate (e.g., rate of gas traversing through the elongated tubes 106 and 108) may be based on a volume of the cell culture or media within the enclosure. For example, the controller 202 may have the gas flow rate be lower (e.g., 0.02 L/min) for enclosures with cell cultures having a lower volume relative to the gas flow rate (e.g., 0.1 L/min) of enclosures having higher volume cell cultures.

It should be noted in other embodiments the bioreactor system 100 may include more than two tubes (e.g., five tubes), for example, the pumping unit 216 may be coupled to one or more tubes (not shown) in contact with the cell culture.

The pumping unit 216 may be configured to move fluid into and out of an enclosure (e.g., the second enclosure 306). For example, the pumping unit 216 may feed media and/or the cell culture from a tank carried by an elongated tube into the enclosure. In another example, the pumping unit 216 may remove waste media from the cell culture carried by an elongated tube to a waste tank. The pumping unit 216 may receive instructions from the controller 202, which determines when to add and/or remove fluid from the enclosure. The pumping unit 216 may be a displacement pump that includes a cavity to create a suction for moving fluid within the pumping unit 216 from a source location (e.g., tank, enclosure) to a discharge location (e.g., enclosure, waste tank). Optionally, the pumping unit 216 may include one or more rotors and/or plungers to move fluid within the pumping unit 216.

Figure 3:
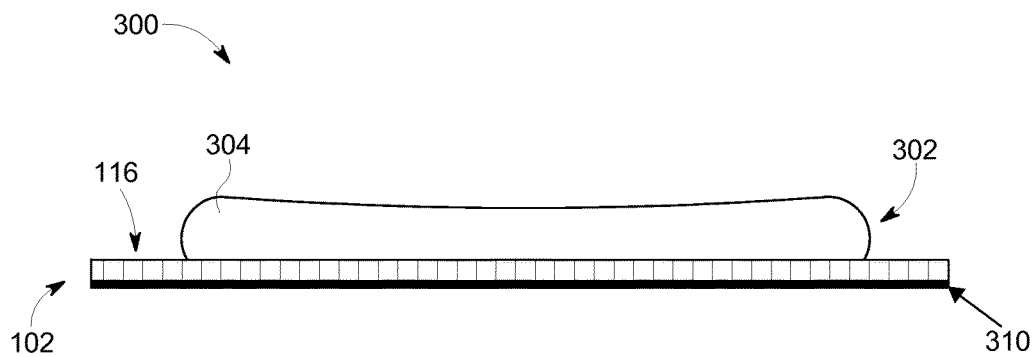
FIG. 3 is an illustration of a cross section of a portion of a bioreactor system, in accordance with an embodiment.

In connection with FIG. 3, the platform heating element 214 corresponds to a heating element 310 controlled by the controller circuit 202 for generating thermal energy on the surface area of the platform 116. For example, the controller circuit 202 may adjust an amount of thermal energy generated by the heating element 310 via regulating the amount of current or voltage delivered to the heating element 310. The heating element 310 may generate thermal energy by providing an impedance or resistance to the current or voltage driven by the controller 202. The heating element 310 may be an etched foil and/or wire that includes Nichrome, Kanthal, Aluminum, Cupronickel, ceramic such as Molybdenum disilicide. and/or the like The controller circuit 202 may adjust the amount of thermal energy generated by the heating element 310 of the platform 102 based on measurements by the temperature sensor 204. For example, the controller circuit 202 may be instructed to have the temperature of the thermal mass.

FIG. 3 is a cross section 300 of the platform 116 with a first enclosure 302. The cross section 300 illustrates the platform heating element 214 or heating element 310 extends under the surface area 116 of the platform 102. As thermal energy is generated by the platform 102 from the heating element 310, heat is conducted along the surface area 116 and is absorbed, generally, by the first enclosure 302.

Optionally, platform 102 may include an insulator (not shown) positioned between the surface area 116 and the heating element 310. The insulator may include a polyurethane foam, silicon foam, cork, vinyl foam, and/or the like. The insulator reduces the transfer and/or flow of thermal energy from the platform 102 to the first enclosure 302. For example, the insulator decreases the thermal conductance efficiency of the platform 102. Generally, the insulator allows only a portion of the heat or thermal energy generated by the heating element 310 to the surface area 116. It should be noted in at least one embodiment, the insulator may be used instead of the first enclosure 302 to control a temperature of the cell culture 312 or media.

The first enclosure 302 may be a flexible container or bag, and is composed of a plastic material. For example, the first enclosure 302 may be formed from layers of polyvinyl chloride and ethyl vinyl acetate. The first enclosure 302 is positioned on top of the platform 102 or adjacent to the surface area 116. The first enclosure 302 may contain a liquid volume, such as one liter, corresponding to the thermal mass 304. It should be noted that in other embodiments the first enclosure 302 may contain more than one liter (e.g., five liters) and or less than one liter of the thermal mass 304.

The thermal mass 304 may include a liquid and/or liquid solution such as water, ethylene glycol, diethylene glycol, ammonia, and/or the like having a large specific heat or thermal capacity. For example, a liquid solution having a specific heat greater than or approximate to three kJ/(kg·K). The thermal mass 304 absorbs at least some or a portion of the thermal energy generated from the heating element 310 of the platform 102 through the first enclosure 302. The thermal energy absorbed by the thermal mass 304 from the heating element 310 results and/or maintains a temperature of the thermal mass 304. For example, increasing the thermal energy generated by the platform 102 may increase a temperature of the thermal mass 304.

Figure 4:
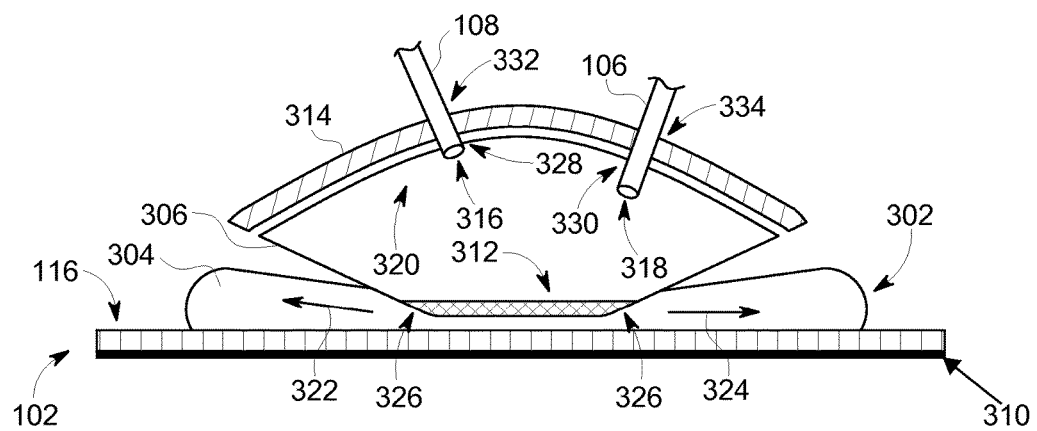
FIG. 4 is an illustration of a cross section of a portion of a bioreactor system, in accordance with an embodiment.

In connection with FIG. 4, a second enclosure 306 is positioned on top of the first enclosure 302. For example the first enclosure 302 is positioned between the second enclosure 306 and the platform 102.

FIG. 4 is a cross section of the platform 116 with the first enclosure 302, the second enclosure 306 and a cover 314. The second enclosure 306 may be a container or bag composed of a plastic material similar to and/or the same as the plastic material of the first enclosure 302. The second enclosure 306 is smaller or can contain a volume smaller than the first enclosure 302. The second enclosure 306 may contain a cell culture 312 (e.g., which includes starter cells and a media) and a gas mixture 320 (e.g., gas filled headspace).

The cell culture 312 is thermally coupled to the thermal mass 304 of the first enclosure 302. The cell culture 312 may be a solution of starter cells (e.g., T cells, Hybridoma cells) combined with a culture medium or media having predetermined attributes to promote growth of the starter cells. For example, the media may include Human AB serum, penicillin-streptomycin, Glutamax, Interleukin 2, NAC, and/or the like. Optionally, the amount of the culture media of the cell culture may be based on the amount of starter cells. For example, one milliliter of culture media may be added for every million starter cells.

The cell culture 312 has a volume less than the thermal mass 304. For example the cell culture 312 may have a volume of less than sixty milliliters. It should be noted that another embodiments the cell culture 312 may have a volume of greater than sixty milliliters and/or less than sixty milliliters (e.g., fifty milliliters).

The gas mixture 320 may be provided by the elongated tubes 106 and 108 through openings 328 and 330, respectively, within the second enclosure 306. The gas mixture 320 may include at least one of nitrogen, oxygen, carbon dioxide, and/or the like that may be used by the starter cells and/or promote metabolism of the starter cells within the cell culture 312. For example, oxygen may be added to the gas mixture 320 through the opening 318 of the elongated tube 106. Concurrently, a portion of the gas mixture 320 is exhausted from the second enclosure 306 via the opening 316 of the elongated tube the 108.

Optionally, opposing ends (not shown) of the elongated tubes 106 and 108, with respect to the ends 316 and 318, may include filters to maintain sterility of the cell culture 312. The filters are configured to prevent external microorganisms from entering the second enclosure 306 during circulation of the gas mixture 320 carried by the elongated tubes 106 and 108. For example, a sterilizing inlet filter may be positioned on the opposing end of the elongated tube 108 and an exhaust filter enclosed by a heater (not shown) may be positioned on the opposing end of the elongated tube 106.

FIG. 4 illustrates the shape of the first enclosure 302 adjusted by the second enclosure 306, 302 relative to the shape of the first enclosure 302 illustrated in FIG. 3, based on a surface area 326 of the second enclosure 306 in contact with the first enclosure 302. For example, the adjusted shape of the first enclosure 302 accommodates and/or form-fits the second enclosure 306. When the second enclosure 306 is placed on the first enclosure 302, a weight of the second enclosure 306 is applied to the first enclosure 302 along the surface area 326 of the second enclosure 306 in contact with the first enclosure 302. The weight of the second enclosure 306 adjusts the shape of the first enclosure 302 by displacing the thermal mass 304 within the first enclosure 302 away from the second enclosure 306, for example, in the direction of arrows 322 and 324. The displacement of the thermal mass 304 allows the shape of the first enclosure 302 to be adjusted.

The cover 314 is positioned on a top surface area of the second enclosure 306. The top surface area of the second enclosure 306 may correspond to a position of the gas mixture 320 within the second enclosure 306 allowing the cover 314 to be thermally coupled to the gas mixture 320 and/or top surface area. Additionally or alternatively, the top surface area of the second enclosure 306 may correspond to portions of the second enclosure 306 not in contact and/or proximate to the first enclosure 302 and/or cell culture 312.

The cover 314 may have a shape conforming to the top surface area of the second enclosure 306, such as a domed and/or curved shape. For example, the shape of the cover 314 may follow and/or conform to the top surface area of the second enclosure 306. Optionally, the cover 314 may be coupled to the second enclosure 306. For example, the cover 314 may be coupled to the second enclosure 306 using glue, adhesive tape, pressure sensitive adhesive, and/or the like. The cover 314 includes openings 332 and 334 aligned with the openings 328 and 330 of the second enclosure 306. The openings 332 and 334 allows the elongated tubes to extend through the openings 332 and 334 of the cover 314 to the second enclosure 306.

Figure 5:
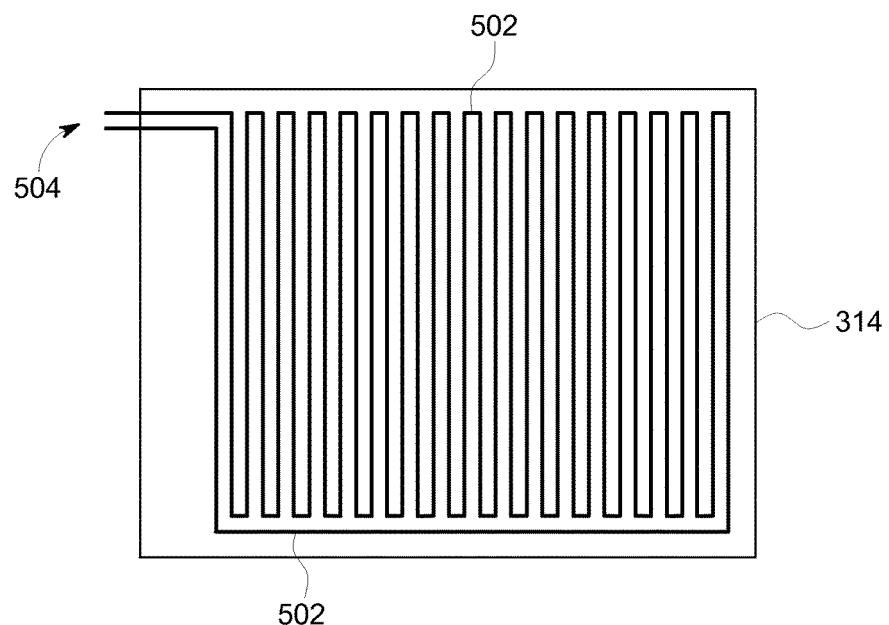
FIG. 5 is a schematic diagram of a portion of a cover, in accordance with an embodiment.

FIG. 5 illustrates a schematic diagram of the cover 314. The cover 314 generates thermal energy via a heating element 502 controlled by the controller circuit 302. For example, the heating element 502 corresponds to the cover heating element 212 of FIG. 2. The heating element 502 may be an etched foil that includes Aluminum, Nickel, platinum and/or the like. Additionally or alternatively, the heating element 502 may be a wire that includes Nichrome, Kanthal, Cupronickel, ceramic such as Molybdenum disilicide, and/or the like. The heating element 502 may extend throughout the cover 314 via traces formed by a substrate of the cover 314. The heating element 502 is enclosed and/or surrounded by the substrate. The heating element 502 may extend evenly within the cover 314 such that the thermal energy generated by the heating element 502 is approximately the same or even throughout the cover 314, within a predetermined threshold. The substrate may be composed of polyimide, silicone rubber, and/or the like.

For example, the substrate may include two polyimide sheets with cavities corresponding to the traces for the heating element 502. The sheets may be coupled together using an epoxy or adhesive forming the cover 314.

The controller circuit 202 may adjust an amount of thermal energy generated by the heating element 502 based on an amount of current or voltage delivered to the heating element 502 via terminals 504. For example, the controller circuit 202 may be electrically coupled to the heating element 502 via the terminals 504. The heating element 502 may generate thermal energy by providing an impedance or resistance to the current or voltage driven by the controller 202. At least a portion of the thermal generated by the heating element 502 of the cover 314 is absorbed by the second enclosure 306, such as a top portion of the second enclosure 306, resulting in and/or to maintain a temperature of the top portion of the second enclosure 306 above the dew point.

Additionally or alternatively, the controller 202 may drive the heating element 502 to generate thermal energy to maintain osmolality at a set threshold (e.g., at and/or below approximately 350 mmol/kg) within the second enclosure 306. For example, the controller 202 may drive the heating element 502 to generate thermal energy above a condensation or dew point within the second enclosure. For example, the dew point within the second enclosure 306 may be at 37 degrees Celsius, corresponding to a temperature at which water vapor from the media of the cell culture 312 condenses along a top surface within the second enclosure 306. As the water within the cell culture 312 reduces due to the condensation, the osmolality within the second enclosure 306 increases. The controller 202 drives the heating element 502 to generate thermal energy, which is at least partially absorbed by the top surface of the second enclosure 306. The thermal energy maintains the temperature of the top surface of the second enclosure 306 above the dew point, such as 38.5 degrees Celsius. It should be noted that in other embodiments the dew point and/or may be higher than or lower than 37 degrees Celsius.

Optionally, the temperature of the top portion of the second enclosure 306 and/or cover 314 based on the thermal energy generated by the cover 314 is higher than the temperature of the thermal mass 304 and/or platform 102 based on the thermal energy generated by the platform 102. For example, a surface temperature of the cover 314 directly adjacent to the second enclosure 306 is greater than the temperature on the surface area 116 of the platform adjacent to the first enclosure 302.

Additionally or alternatively, the controller 202 may adjust the thermal energy generated by the cover 314 based on the sensor 204 of FIG. 2. For example, the sensor 204 may be positioned proximate to and/or in contact with the top surface area of the second enclosure 306. The temperature measurements of the sensor 204 may be received by the control 202 and/or compared by the controller 202 to a predetermined cover temperature threshold. The predetermined cover temperature threshold may be set above the dew point within the second enclosure 306. Based on the temperature measurements of the sensor 204 with respect to the predetermined cover temperature threshold, the controller 202 may increase and/or decrease the amount of thermal energy generated by the cover 314.

Figure 6:
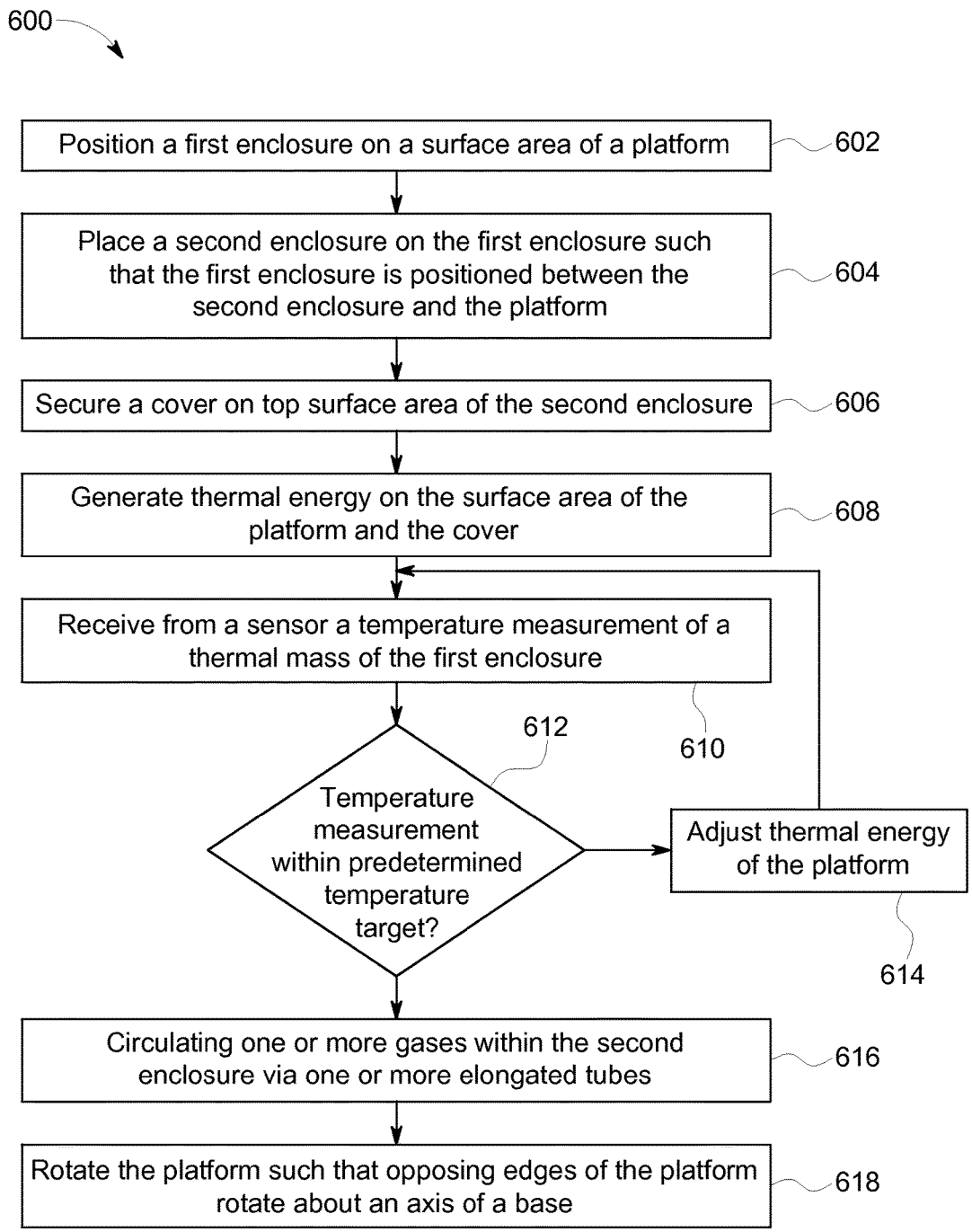
FIG. 6 is a flowchart of a method for initiating a cell culture, in accordance with an embodiment.

FIG. 6 illustrates a flowchart of a method 600 for initiating a cell culture using a conventional bioreactor. The method 600, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 600 may be used as one or more algorithms to direct hardware to perform one or more operations described herein. It should be noted, other methods may be used, in accordance with embodiments herein.

One or more methods may (i) position a first enclosure on a surface area of a platform, (ii) place a second enclosure on the first enclosure such that the first enclosure is positioned between the second enclosure in the platform, (iii) secure a cover on a top surface area of the second enclosure, (iv) generate thermal energy on the surface area of the platform and the cover.

Beginning at 602, the first enclosure 302, containing the thermal mass 304, is positioned on the surface area 116 of the platform 102. For example, the first enclosure 302 is placed adjacent to the surface area 116 of the platform 102, which may thermally couple the thermal mass 302 to the platform 102.

At 604, the second enclosure 306 is placed on the first enclosure 302 such that the first enclosure 302 is positioned between the second enclosure 306 and the platform 102. When the second enclosure 306 is placed on the first enclosure 302, a shape of the first enclosure 302 may be adjust and/or conform to the surface area 326 of the second enclosure in contact with the first enclosure 302. For example, a portion of the thermal mass 304 may be displaced within the first enclosure 302 surrounding the cell culture 312 within the second enclosure 306, thermally coupling the thermal mass 304 to the cell culture 312.

At 606, the cover 314 is secured on the top surface area of the second enclosure 306. For example, the cover 314 may have a dome or curved shape corresponding to a shape of the top surface area of the second enclosure 306. Additionally or alternatively, the cover 314 may be coupled to the top surface area of the second enclosure 306 via glue, adhesive tape, and/or the like. Optionally, an insulator may be placed over the cover 314.

At 608, thermal energy is generated on the surface area 116 of the platform 102 and the cover 314. For example, first and second thermal energy may be generated by heating elements 310 and 502 of the platform 102 and the cover 314, respectively. The amount of first and second thermal energy generated by the heating elements 310 and 502, respectively, may be determined and/or controlled by the controller 202. For example, the controller 202 may control an amount of current and/or voltage to the heating elements 310 and 502 (e.g., platform heating element 214, cover heating element 212) which is used to generate the first and second thermal energy of the heating elements 310 and 502.

At 610, the controller 202 may receive temperature measurements of the thermal mass 304 of the first enclosure 302 from the sensor 204. For example, the sensor 204 may be positioned proximate and/or adjacent to the first enclosure 302. The thermal mass 304 absorbs at least some of the first thermal energy generated by the platform 102 resulting in a temperature of the thermal mass 304. The sensor 204 may acquire temperature measurements corresponding to a temperature of the thermal mass 304, and are received by the controller 202. Optionally, an additional temperature sensor may be used to measure a temperature of the cover 314 and/or the top surface of the second enclosure 306.

At 612, the controller 202 may determine whether the temperature measurement is within a predetermined temperature target. The predetermined temperature target may be stored on the memory 210. Optionally, the predetermined temperature target may be received by the controller 202 from the user interface 110. The predetermined temperature target may correspond to a temperature approximate to a desired temperature of the cell culture 312. The controller 202 may compare the temperature measurement acquired by the sensor 204 to the predetermined temperature target. Based on a difference between a value of the temperature measurement and the predetermined temperature target, the controller 202 can determine whether the thermal mass 304 is at the desired temperature.

For example, the predetermined temperature target may be set at 37.5 degrees Celsius. The controller 202 may determine that temperature measurements not within 0.2 degrees of the predetermined temperature target, such as greater than 37.9 degrees Celsius or less than 37.3 degrees Celsius are determined not to be within the predetermined temperature target.

If the temperature measurement is determined by the controller 202 to not be within the predetermined temperature target, then at 614, the controller 202 adjusts the thermal energy generated by the platform 102. For example, if the temperature measurement from the sensor 204 is below the predetermined temperature target, the controller 202 may increase the current or voltage to the heating element 310. Thereby, increasing the thermal energy generated by the platform 102. In another example, if the temperature measurement from the sensor 204 is above the predetermined temperature target, the controller 202 may decrease the current or voltage to the heating element 310. Thereby, decreasing the thermal energy generated by the platform 102.

If the temperature measurement is determined by the controller 202 to be within the predetermined temperature target, then at 616, one or more gases are circulated within the second enclosure 306 via the one or more elongated tubes 106 and 108. For example, the controller 202 may instruct the gas flow interface 208 to inject one or more gases into the second enclosure 306, and exhaust one or more gases from the second enclosure 306 via the elongated tubes 106 and 108 respectively. The one or more gases may include nitrogen, oxygen, carbon dioxide, and/or the like. The controller 202 may determine the proportion of gases injected and/or exhausted from the second enclosure 306 based on a predetermined setting stored on the memory 210. Additionally or alternatively, the proportion of gases may be received by the controller 202 based on inputs received by the user interface 110.

At 618, the platform 102 is rotated such that opposing edges 122 and 124 of the platform 102 rotate about the axis 120 of the base 112. For example, the controller 202 may enable and/or instruct the motor 206 to rock back and forth across the pivot point 104. A rocking speed and angle of the platform 102 during rotation about the axis 120 may be determined by the controller 202 from predetermined settings store on the memory 210. Additionally or alternatively, the rocking speed and angle of the platform 102 may be received by the controller 202 based on inputs received by the user interface 110.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a structure, limitation, or element that is "configured to" perform a task or operation may be particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optic drive, and the like. The storage device may also be other similar means for loading computer programs or other instructions into the computer or processor.

As used herein, the term "computer," "controller," and "module" may each include any processor-based or microprocessor-based system including systems using microcontrollers, reduced instruction set computers (RISC), application specific integrated circuits (ASICs), logic circuits, GPUs, FPGAs, and any other circuit or processor capable of executing the functions described herein. The above examples are exemplary only, and are thus not intended to limit in any way the definition and/or meaning of the term "module" or "computer."

The computer, module, or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, module, or processor as a processing machine to perform specific operations such as the methods and processes of the various embodiments described and/or illustrated herein. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program. The individual components of the various embodiments may be virtualized and hosted by a cloud type computational environment, for example to allow for dynamic allocation of computational power, without requiring the user concerning the location, configuration, and/or specific hardware of the computer system.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

This written description uses examples to disclose the various embodiments, and also to enable a person having ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

The foregoing description of certain embodiments of the present inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, or the like). Similarly, the programs may be stand alone programs, may be incorporated as subroutines in an operating system, may be functions in an installed software package, or the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "comprises," "including," "includes," "having," or "has" an element or a plurality of elements having a particular property may include additional such elements not having that property.

What is claimed is:

1. A bioreactor system for culturing cells, comprising:
   a platform, wherein the platform comprises a platform heating element for generating first thermal energy on a surface area of the platform;
   a first enclosure containing a thermal mass, wherein the first enclosure is positioned adjacent to the surface area, the thermal mass absorbing at least some of the first thermal energy from the platform;
   a second enclosure containing a culture fluid and a gas mixture, wherein the first enclosure is positioned between the second enclosure and the platform, the thermal mass of the first enclosure is thermally coupled to the culture fluid; and
   a cover positioned adjacent to the second enclosure, wherein the cover comprises a cover heating element for generating second thermal energy and the cover is thermally coupled to the second enclosure, wherein the second enclosure is positioned between the first enclosure and the cover.

2. The bioreactor system of claim 1, wherein the first enclosure, the second enclosure and the cover are operatively coupled to each other such that at least a portion of the first thermal energy is absorbed by the thermal mass of the first enclosure resulting in a first temperature of the thermal mass, and at least a portion of the second thermal energy generated by the cover is absorbed by a top portion of the second enclosure resulting in a second temperature of the top portion, the second temperature being higher than the first temperature.

3. The bioreactor system of claim 1, further comprising a temperature sensor that measures a temperature of the thermal mass.

4. The bioreactor system of claim 3, further comprising a controller that determines an amount of the first thermal energy generated by the platform, wherein the controller determines the amount of the first thermal energy based on the temperature measured by the temperature sensor.

5. The bioreactor system of claim 1, wherein the second enclosure includes a first opening and the cover includes a second opening, the first and second openings are aligned with respect to each other; and
further comprising a plurality of elongated tubes extending through the first opening and the second opening.

6. The bioreactor system of claim 5, further comprising one or more tanks coupled to the elongated tubes, wherein at least one of nitrogen, oxygen, or carbon dioxide is carried from the one or more tanks through one of the elongated tubes.

7. The bioreactor system of claim 5, further comprising a gas flow interface circulating the gas flow within the second enclosure between the elongated tubes at a gas flow rate, wherein the gas flow rate is based on a volume of the culture fluid.

8. The bioreactor system of claim 1, further comprising a controller determining an amount of the second thermal energy generated by the cover, wherein the controller determines the amount of the second thermal energy based on a dew point within the second enclosure.

9. The bioreactor system of claim 1, wherein a shape of the first enclosure is adjusted by the second enclosure based on a surface area of the second enclosure in contact with the first enclosure.

10. The bioreactor system of claim 1, wherein the thermal mass includes at least one of water, ethylene glycol, diethylene glycol, or ammonia.

11. The bioreactor system of claim 1, further comprising a base, wherein the platform is pivotably mounted on the base such that opposing edges of the platform rotate about an axis of the base.

12. The bioreactor system of claim 11, further comprising a motor configured to rock the platform about the axis of the base.

13. The bioreactor system of claim 1, wherein the second enclosure is configured to contain the culture fluid of a volume of less than sixty milliliters.

14. The bioreactor system of claim 1, wherein the second enclosure is smaller in volume than the first enclosure.

15. A method of operating a bioreactor system for culturing cells, comprising:
positioning a first enclosure on a surface area of a platform, wherein the first enclosure contains a thermal mass and the platform comprises a platform heating element;
placing a second enclosure on the first enclosure such that the first enclosure is positioned between the second enclosure and the platform, the second enclosure containing a culture fluid and a gas mixture;
securing a cover on the second enclosure such that the cover is positioned adjacent to the second enclosure, wherein the cover comprises a cover heating element;
generating first thermal energy on the surface area of the platform from the platform heating element and second thermal energy from the cover using the cover heating element, wherein a second temperature of the cover based from the second thermal energy is greater than a first temperature of the platform based from the first thermal energy; and
culturing cells in the culture fluid of the second enclosure.

16. The method of claim 15, further comprising:
receiving from a sensor a temperature measurement of the thermal mass; and
adjusting the first thermal energy generated by the platform based on the temperature measurement.

17. The method of claim 15, further comprising circulating at least one of nitrogen, oxygen, or carbon dioxide within the second enclosure via one or more elongated tubes, wherein the one or more elongated tubes extend through the cover and the second enclosure.

18. The method of claim 15, further comprising rotating the platform such that opposing edges of the platform rotate about an axis of a base, wherein the platform is pivotably mounted on the base.

19. The method of claim 15, wherein the culture fluid has a volume of less than sixty milliliters.

20. A bioreactor system for culturing cells, comprising:
a platform pivotably mounted on a base such that opposing edges of the platform rotate about an axis of the base resulting in a rocking motion, wherein the platform comprises a platform heating element for generating first thermal energy on a surface area of the platform during the rocking motion;
a first enclosure containing a thermal mass, wherein the first enclosure is positioned adjacent to the surface area of the platform, the thermal mass absorbing at least some of the first thermal energy generated from the platform;
a second enclosure containing a culture fluid and a gas mixture, wherein the first enclosure is positioned between the second enclosure and the platform, the thermal mass thermally coupled to the culture fluid such that the culture fluid absorbs at least some of thermal energy from the first enclosure; and
a cover positioned adjacent to the second enclosure and disposed on a top surface area of the second enclosure such that the cover is thermally coupled to the gas mixture, wherein the cover comprises a cover heating element for generating second thermal energy, at least some of the second thermal energy being absorbed by the second enclosure, and wherein the second enclosure is positioned between the first enclosure and the cover.

* * * * *